US008706436B2

(12) United States Patent
Rose et al.

(10) Patent No.: US 8,706,436 B2
(45) Date of Patent: Apr. 22, 2014

(54) MANUFACTURE OF ENGINEERING COMPONENTS WITH DESIGNED DEFECTS FOR ANALYSIS OF PRODUCTION COMPONENTS

(75) Inventors: Curtis Wayne Rose, Mechanicville, NY (US); John Broddus Deaton, Jr., Niskayuna, NY (US)

(73) Assignee: General Electric Company, Schenectady, NY (US)

(*) Notice: Subject to any disclaimer, the term of this patent is extended or adjusted under 35 U.S.C. 154(b) by 362 days.

(21) Appl. No.: 13/152,489

(22) Filed: Jun. 3, 2011

(65) Prior Publication Data

US 2012/0310576 A1 Dec. 6, 2012

(51) Int. Cl.
*G06F 19/00* (2011.01)
*G01N 29/44* (2006.01)
*G05B 19/401* (2006.01)

(52) U.S. Cl.
CPC .......... *G01N 29/4436* (2013.01); *G05B 19/401* (2013.01)
USPC ............................................. 702/83; 702/185

(58) Field of Classification Search
CPC .......................... G06F 17/50; G01N 29/4436
USPC ............................................................ 702/83
See application file for complete search history.

(56) References Cited

U.S. PATENT DOCUMENTS

2007/0162257 A1\* 7/2007 Kostyk et al. ................. 702/182
2008/0300888 A1\* 12/2008 Dell'Anno et al. ............... 705/1

\* cited by examiner

*Primary Examiner* — Bryan Bui
(74) *Attorney, Agent, or Firm* — Hoffman Warnick LLC

(57) ABSTRACT

An engineering component with a designed defect and use of an engineering component with a designed defect to evaluate a production component are disclosed. A test component having a known defect is manufactured. This known defect is a flaw that is intentionally included in the test component. The test component is then analyzed to obtain a test profile of the defect. In addition, the engineering component to be tested is analyzed to obtain a production profile. This production profile is compared with the test profile to determine whether the engineering component has a defect that corresponds to the known defect.

17 Claims, 6 Drawing Sheets

MANUFACTURE OF ENGINEERING COMPONENTS WITH DESIGNED DEFECTS FOR ANALYSIS OF PRODUCTION COMPONENTS

BACKGROUND OF THE INVENTION

The subject matter disclosed herein relates generally to component testing/evaluation. More specifically, the present invention relates to testing/evaluation of a component using components that have been manufactured with designed defects.

In a complex machine, a number of components having varying sizes, shapes and functions work together to accomplish the purpose for which the machine has been designed. However, a failure of a component can cause the entire machine to function incorrectly or to cease operating altogether.

Sometimes, component failure is brought on by one or more defects in the component. These defects can occur in original manufacturing of the component, can be caused by operational stresses in conjunction with the machine or can involve various other factors. Sometimes, these defects can be detected in the component prior to failure of the component. However, it is difficult to know, simply based on the character of the detected defect, whether failure is imminent and the part must be replaced, or, in the alternative, whether the observed defect has little or no impact on the operation of the component within the machine. As such, a component with a detected defect may be unnecessarily replaced or may be allowed to remain in operation until it fails, each of which can consume unnecessary time and/or resources.

BRIEF DESCRIPTION OF THE INVENTION

An engineering component with a designed defect and use of an engineering component with a designed defect to evaluate a production component are disclosed. A test component having a known defect is manufactured. This known defect is a flaw that is intentionally included in the test component. The test component is then analyzed to obtain a test profile of the defect. In addition, the engineering component to be tested is analyzed to obtain a production profile. This production profile is compared with the test profile to determine whether the engineering component has a defect that corresponds to the known defect.

A first aspect of the invention provides a method for analyzing an engineering component, comprising: manufacturing a test component having a known defect, the known defect being a flaw that is intentionally included in the test component; analyzing the test component to obtain a test profile of the defect; analyzing the engineering component to obtain a production profile; and comparing the production profile and the test profile to determine whether the engineering component has a defect that corresponds to the known defect.

A second aspect of the invention provides a system for analyzing an engineering component, comprising: a test component manufactured having a known defect, the known defect being a flaw that is intentionally included in the test component; an analyzer that analyzes the test component to obtain a test profile of the defect and analyzes the engineering component to obtain a production profile; and a comparator that compares the production profile and the test profile to determine whether the engineering component has a defect that corresponds to the known defect.

A third aspect of the invention provides a program product stored on a computer readable storage medium for analyzing an engineering component, which when executed by a computer performs a method, comprising: directing a manufacture of a test component having a known defect, the known defect being a flaw that is intentionally included in the test component; analyzing the test component to obtain a test profile of the defect; analyzing the engineering component to obtain a production profile; and comparing the production profile and the test profile to determine whether the engineering component has a defect that corresponds to the known defect.

BRIEF DESCRIPTION OF THE DRAWING

These and other features of the disclosure will be more readily understood from the following detailed description of the various aspects of the invention taken in conjunction with the accompanying drawing that depict various aspects of the invention, in which.

DETAILED DESCRIPTION OF THE INVENTION

An engineering component with a designed defect and use of an engineering component with a designed defect to evaluate a production component are disclosed. A test component having a known defect is manufactured. This known defect is a flaw that is intentionally included in the test component. The test component is then analyzed to obtain a test profile of the defect. In addition, the engineering component to be tested is analyzed to obtain a production profile. This production profile is compared with the test profile to determine whether the engineering component has a defect that corresponds to the known defect.

Figure 1:
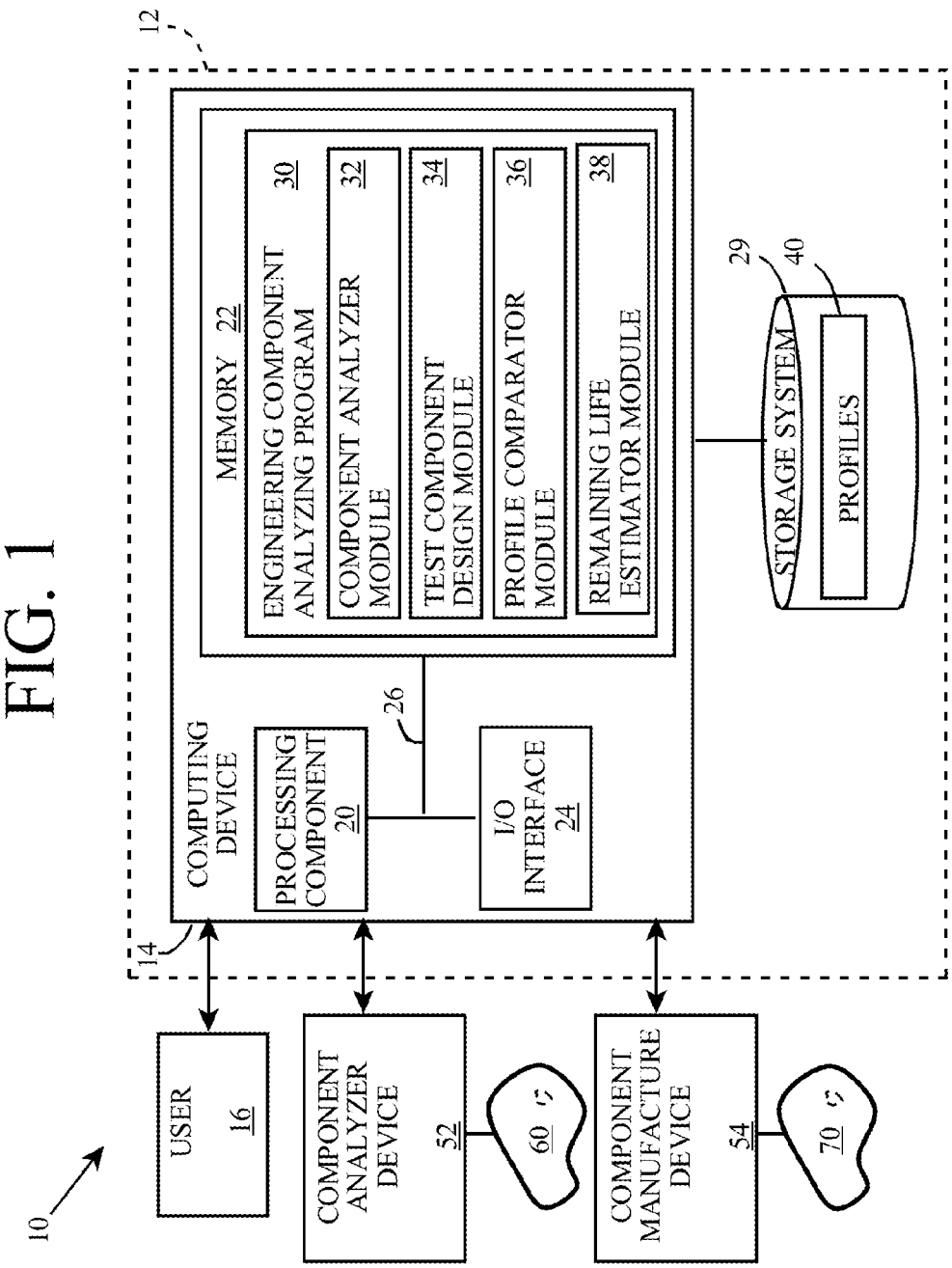
FIG. 1 shows an illustrative environment for analyzing an engineering component pursuant to an embodiment of the invention.

Turning to the drawings, FIG. 1 shows an illustrative environment 10 for analyzing an engineering component 60 according to an embodiment. To this extent, environment 10 includes a computer system 12 that can perform a process described herein in order to analyze an engineering component 60. In particular, computer system 12 is shown including a computing device 14 that includes an engineering component analyzing program 30, which makes computing device 14 operable to analyze an engineering component 60 by performing a process described herein.

Computing device 14 is shown including a processing component 20 (e.g., one or more processors), a memory 22, a storage system 29 (e.g., a storage hierarchy), an input/output (I/O) interface component 24 (e.g., one or more I/O interfaces and/or devices), and a communications pathway 26. In general, processing component 20 executes program code, such as engineering component analyzing program 30, which is at least partially fixed in memory 22. While executing program code, processing component 20 can process data, which can result in reading and/or writing transformed data from/to memory 22 and/or I/O interface component 24 for further processing. Pathway 26 provides a communications link between each of the components in computer system 12. I/O interface component 24 can comprise one or more peripheral I/O devices, which enable communications between a peripheral device, such as component analyzer device 52 and/or component manufacture device 54. Additionally, or in the alternative, I/O interface component 24 can comprise one or more human I/O devices, which enable a human user 16 to interact with computer system 12 and/or one or more communications devices to enable a system user 16 to communicate with computer system 12 using any type of communications link. To this extent, engineering component analyzing program 30 can manage a set of interfaces (e.g., graphical user interface(s), application program interface, and/or the like) that enable human and/or system users 16 to interact with engineering component analyzing program 30. Further, engineering component analyzing program 30 can manage (e.g., store, retrieve, create, manipulate, organize, present, etc.) the data, such as profiles 40, using any solution.

In any event, computer system 12 can comprise one or more general purpose computing articles of manufacture 14 (e.g., computing devices) capable of executing program code, such as engineering component analyzing program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, engineering component analyzing program 30 can be embodied as any combination of system software and/or application software. In any event, the technical effect of computer system 12 is to provide processing instructions to computing device 14 in order to analyze an engineering component 60.

Further, engineering component analyzing program 30 can be implemented using a set of modules 32-38. In this case, a module 32-38 can enable computer system 12 to perform a set of tasks used by engineering component analyzing program 30, and can be separately developed and/or implemented apart from other portions of engineering component analyzing program 30. As used herein, the term "component", when used as an element of computer system 12, means any configuration of hardware, with or without software, which implements the functionality described in conjunction therewith using any solution, while the term "module" means program code that enables a computer system 12 to implement the actions described in conjunction therewith using any solution. When fixed in a memory 22 of a computer system 12 that includes a processing component 20, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computer system 12.

When computer system 12 comprises multiple computing devices 14, each computing device can have only a portion of engineering component analyzing program 30 fixed thereon (e.g., one or more modules 32-38). However, it is understood that computer system 12 and engineering component analyzing program 30 are only representative of various possible equivalent computer systems that may perform a process described herein. To this extent, in other embodiments, the functionality provided by computer system 12 and engineering component analyzing program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 12 includes multiple computing devices 14, the computing devices can communicate over any type of communications link. Further, while performing a process described herein, computer system 12 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, engineering component analyzing program 30 enables computer system 20 to analyze an engineering component 60. To this extent, engineering component analyzing program 30 is shown including a component analyzer module 32, a test component design module 34, a profile comparator module 36, and a remaining life estimator module 38.

Referring still to FIG. 1, computer system 12 (e.g., component analyzer module 32) analyzes an engineering component 60. In performing its analysis of engineering component 60, component analyzer module 32 can utilize data obtained via a component analyzer device 52. Component analyzer device 52 can analyze engineering component 60 using solutions that include, but are not limited to acoustics, ultrasound, x-rays, radiography, electromagnetic effects, eddy currents, magnetic particles, liquid penetrant, enhanced vision or any other solution known in the art for measuring the internal and/or external geometry of an object having the composition of engineering component 60. In any case, the analysis of engineering component 60 can yield a profile 40 that corresponds to the specific engineering component 60.

Figure 2:
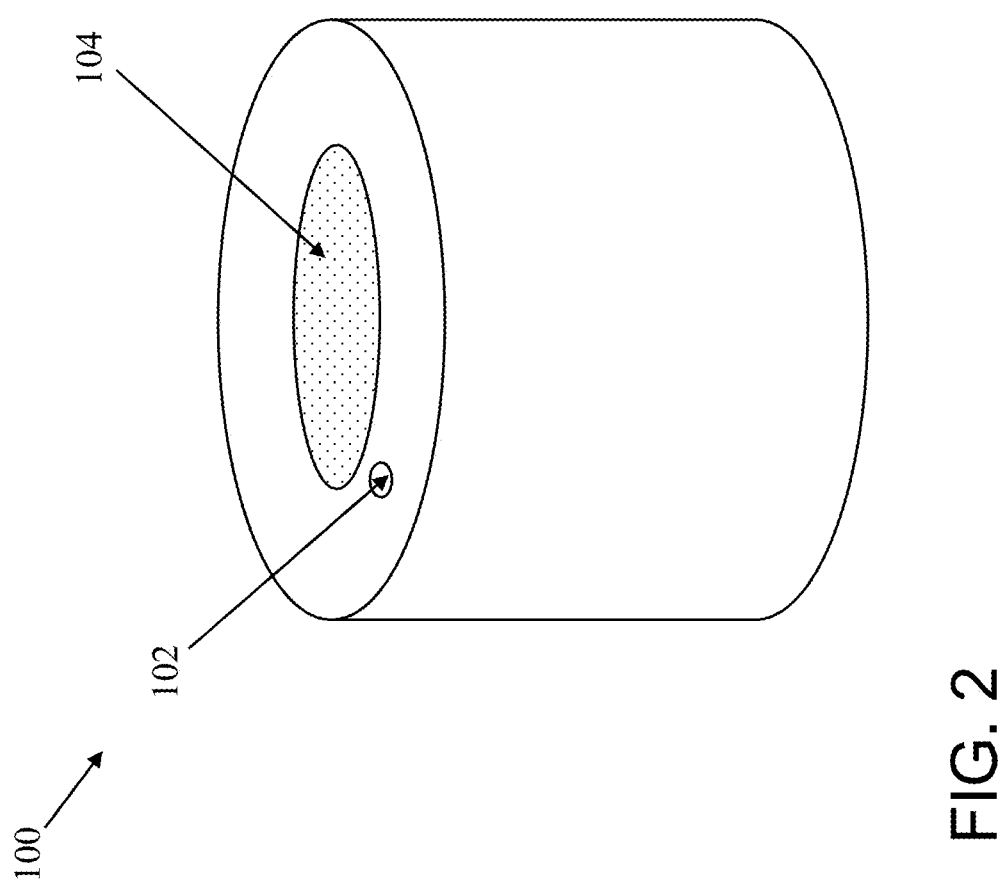
FIG. 2 shows an example engineering component according to an embodiment of the invention.

FIG. 2 shows an example engineering component 100 according to an embodiment of the invention. Engineering component 100 can include any component that forms an element of a complex machine. Specifically, engineering component 100 can be any component for which operational failure could occur. To this extent, engineering component could include any component of a power generation system, including but not limited to a gas turbine, a steam turbine, a generator, a wind turbine, an internal combustion engine, etc. In the alternative, engineering component 100 could be used in an implementation that includes non-power generation applications, including, but not limited to transportation, aviation, industrial applications, appliances, light machinery, heavy machinery, etc. As shown, engineering component 100 is cylindrical in shape with a centrally located aperture 104 and a manufactured indention 102. It should be recognized, however, by those skilled in the art that this configuration is only being used for the purposes of illustration, and, as such, engineering component 100 can assume any shape or size as may be fitting for a component in a complex machine. Similarly, engineering component 100 can comprise any material or combination of materials that can be used to make a component for a complex machine, including, but not limited to metal, metallic alloy, wood, plastic, rubber, ceramics, etc. In any case, as illustrated, engineering component 100 contains substantially no defects. To this extent, an analysis of engineering component 100 using component analyzer device 52 to collect data for component analyzer module 32 can provide a baseline profile for future use in conjunction with a component having a composition that is similar to engineering component 100.

Figure 3:
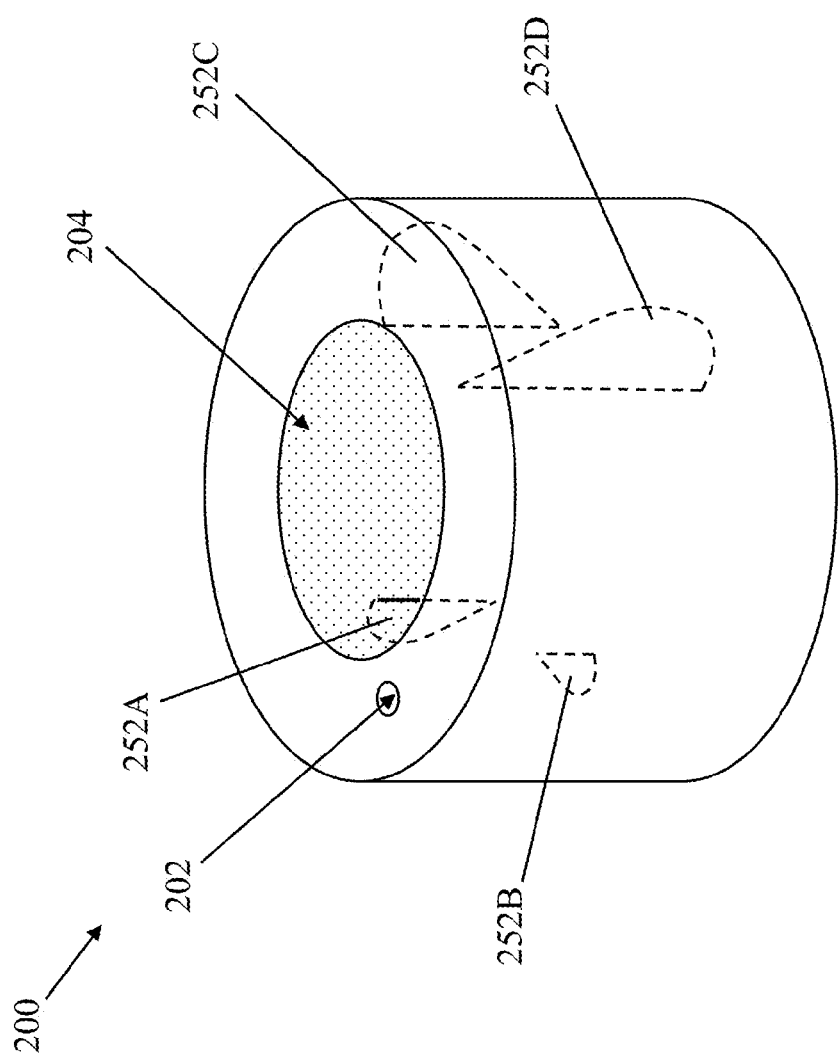
FIG. 3 shows an example flawed component according to an embodiment of the invention.

Turning now to FIG. 3, a flawed component 200 is shown. As illustrated, flawed component 200 has overall characteristics that are substantially the same as engineering component 100, with an aperture 204 and an indention 202 that are similar to those 104, 102, respectively, of engineering component 100. In addition, flawed component 200 includes a number of defects 252A-D oriented about the periphery of aperture 204. Defects 252A-D can be attributed to various causes, including, but not limited to stress, wear, corrosion and/or manufacturing defects. It should be understood that defects 252A-D are not limited to the sizes, shapes, locations and/or orientations illustrated herein. Further, it should be noted that defects 252A-D could occur wholly on a surface of flawed component 200, could be partially submerged within flawed component 200 or could be completely submerged within flawed component 200. In any case, an analysis of engineering component 200 using component analyzer device 52 to collect data for component analyzer module 32 can provide a production profile of flawed component 200 having data that includes attributes that represent defects 252A-D.

Turning again to FIG. 1, computer system 12 (e.g., test component design module 34) directs the manufacture of a test component 70. In performing the manufacturing of test component 70, test component design module 34 can utilize a component manufacture device 54. In one embodiment, one or more designed defects will be manufactured into test component 70 simultaneous with the manufacture of the component itself. In this embodiment, component manufacture device 54 can direct the manufacture of test component 70 using an additive manufacturing process, in which the component is fabricated incrementally, such as by the application of a number of layers in succession. To this extent, component manufacture device 54 can manufacture test component 70 containing one or more designed defects using additive manufacturing solutions that include, but are not limited to laser sintering, stereolithography, electron beam melting, 3D printing, and/or laser net shape cladding. Additionally, component manufacture device 54 can include any device for conventional subtractive manufacturing a component of a complex machine now known or later developed, including, but not limited to, a cutting device, drill, router, mill, lathe, fastening device, etc., used in addition to and/or combination with the additive manufacturing process. To this extent, it should be recognized by one skilled in the art that any process now known or later developed that enables the manufacture of designed defects of general characteristics simultaneous with the manufacture of the component itself can be used to manufacture test component 70. In one embodiment, component manufacture device 54 can include a device used for a laser sintering type additive manufacturing process in which test component 70 can be manufactured by depositing layers of material in succession to form test component 70.

In any case, test component design module 34 can direct component manufacture device 54 in manufacturing test component 60 using profiles 40. As stated above, profiles 40 can include data that has been gained from the analysis of flawed component 200. Elements of the data used to generate these profiles can be stored in storage system 29 and later used singly or in combination to create a particular profile 40. Additionally, or in the alternative, user 16 can create a particular profile 40 using data that represents anticipated flaws in production component 200. This data can be obtained, such as by use of computerized simulations, in service experiments, and/or analysis that yields known or anticipated regions of stress, among others. In this case, user 16 could provide test component design module with all or a part of the data for a particular profile 40, such as via a computer aided design (CAD) application. This profile 40 can then be merged with the profile of a baseline component, such as engineering component 100, or a component that is otherwise flawed to yield a test engineering component having the desired known defect.

Figure 4:
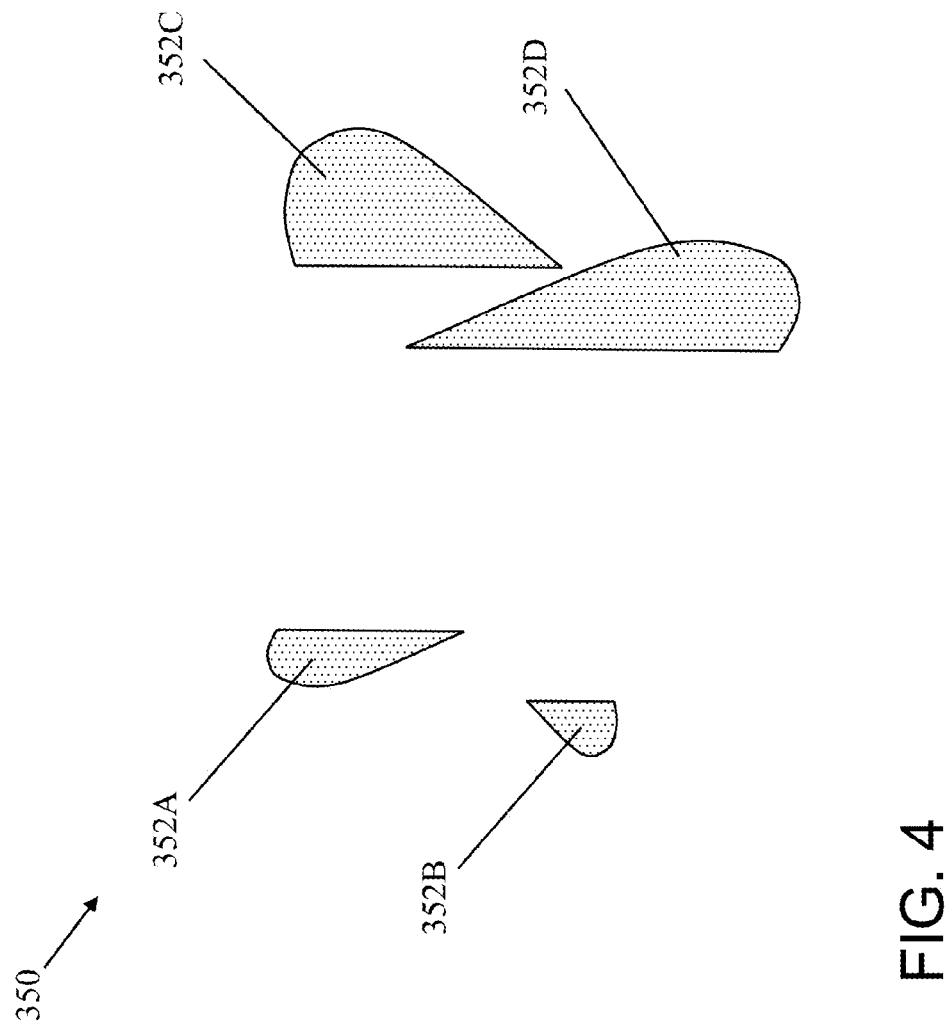
FIG. 4 shows a graphical representation of defects for inclusion into a test component according to an embodiment of the invention.

Turning now to FIG. 4, a graphical representation 350 of defects 352A-D for inclusion into test component 70 (FIG. 1) is shown. As illustrated, defects 352A-D replicate defects 252A-D of flawed component 200 of FIG. 3. To this extent, defects 352A-D could be retrieved from one or more profiles 40 that have been created based on the analysis of flawed component 200 by component analyzer module 32. Additionally, or in the alternative, defects 352A-D could be provided by user 16 and combined with data reflecting a (baseline) non-flawed test component and/or one or more profiles 40 that have been created based on the analysis of a baseline production component, such as engineering component 100, by component analyzer module 32.

Figure 5:
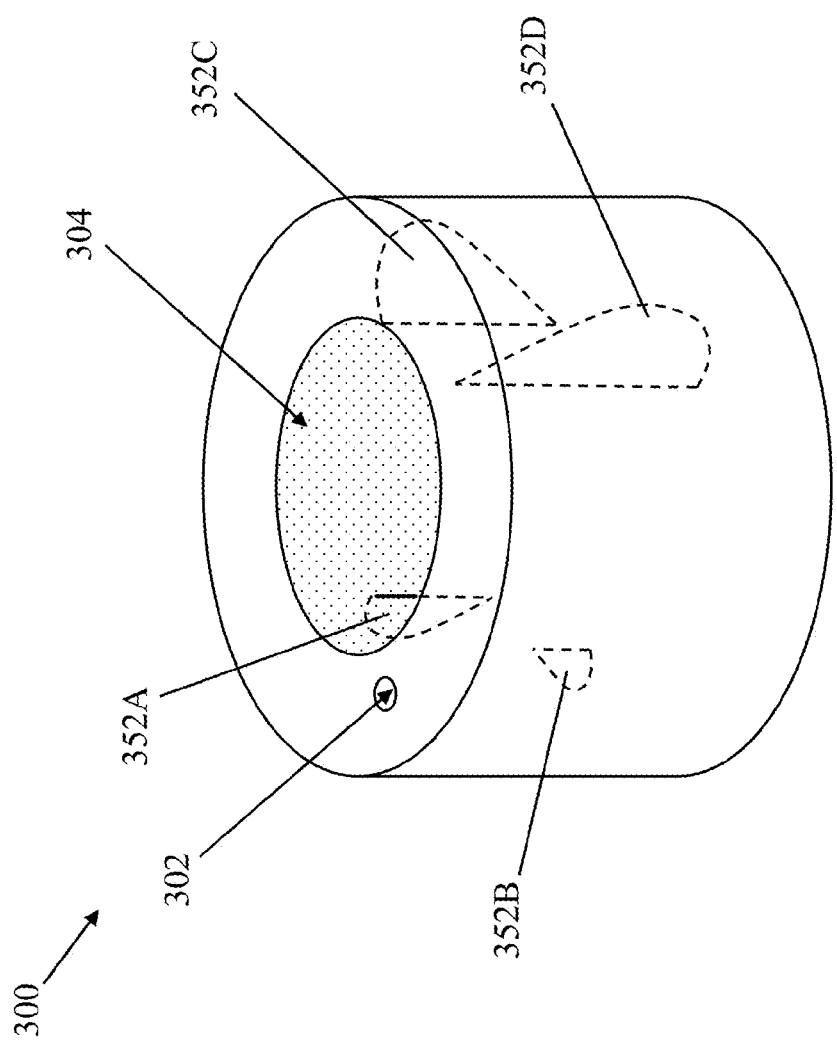
FIG. 5 shows a test component with a known defect pursuant to an embodiment of the invention.

In any case, referring now to FIG. 5, one result of the manufacturing that is directed by test component design module 34 (FIG. 1) includes a manufactured test component 300 having at least one known defect 352A-D. As should be appreciated by one known in the art, defects 352A-D are flaws that have been intentionally introduced into test component 300 during manufacture. To this extent, as illustrated test component 300 is a replica of flawed component 200. However, it should be understood by those skilled in the art that this need not be the case. Rather, defects 352A-D in test component 300 could have differing attributes, such as shape, size, location, and/or orientation from those in flawed component 200. Further, test component 300 may have base attributes, such as shape, size, etc., that differ from those of flawed component 200 into which defects 352A-D are incorporated.

Referring back to FIG. 1, after test component 70 has been manufactured, computer system 12 (e.g., component analyzer module 32) can analyze test component 70. As a result, a test profile of test component 70 that includes defects 352A-D (FIG. 5) can be obtained. This test profile can include data that can be correlated with the attributes of defects 352A-D because the attributes of defects 352A-D, e.g., size, shape, orientation, location, etc., are already known from the manufacturing process. For example, the test profile can be compared to a baseline profile for the component. In this example, any differences in the profiles would be attributed to the defects, the attributes of which are known from the design and/or manufacturing process.

Figure 6:
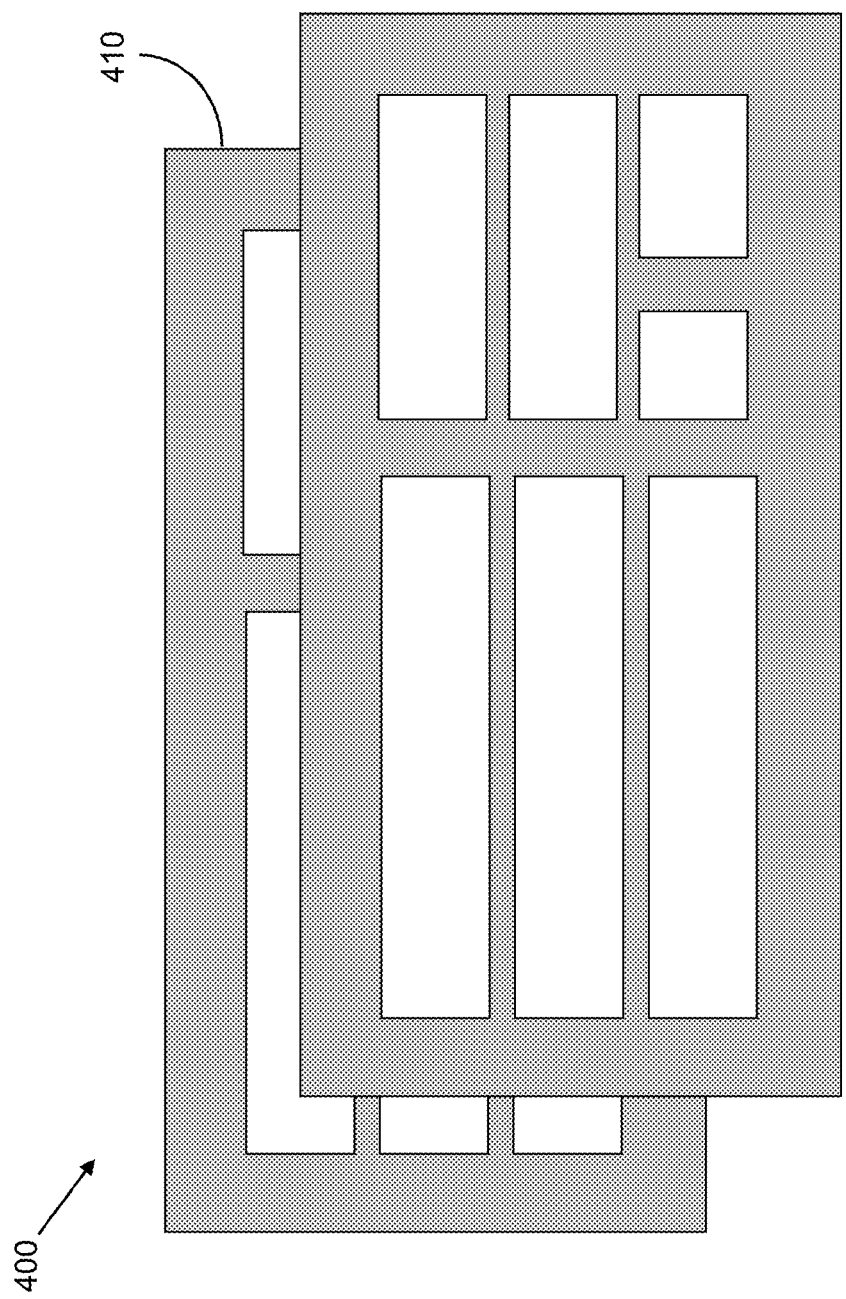
FIG. 6 shows a profiles database pursuant to an embodiment of the invention.

Referring now to FIG. 6 in conjunction with FIG. 1, the test profile obtained from analysis of test component 70 can be stored in a test profiles database 400. Test profiles database 400 can be merged with the storage of other profiles 40 or, in the alternative, can be a separate storage location. In any event, records 410 of test profiles database 400, can store, in addition to the test profile of test component 70, other test profiles. To this extent, every test profile in test profiles database 400 can correspond to a distinct test defect or defects in conjunction with or, in the alternative, in isolation from a distinct test component.

Referring back to FIG. 1, in conjunction with FIGS. 2, 3, 5 and 6, computer system 12 (e.g., profile comparator module 36) can compare the profile of production component 60 with the profile of test component 70. To make this comparison, profile comparator module 36, can retrieve the profile corresponding to test component 70 from test profiles database 400. For example, a comparison by profile comparator module 36 of the profile of test component 300 with the profile of engineering component 100 would not produce a match. Accordingly, profile comparator module 36 would determine that production component 100 does not have a defect that corresponds to defects 352A-D in test component. Conversely, a comparison by profile comparator module 36 that compares the test profile of test component 300 with the profile of flawed component 200 would produce a match. Thus, profile comparator module 36 would determine that flawed component 300 has a defect that corresponds to known defects 352A-D in test component.

In this way, a production component 60, about which user 16 is concerned may be at risk, can be analyzed and tested for defects. For example, user 16 may choose to analyze a component 60 that is beginning to show signs of wear. Alternatively, user 16 may choose to analyze a component 60 that does not show signs of wear on its particular machine but about which user knows that a corresponding component 60 on another machine has failed. In any case, once a profile is generated for production component 60, the profiles in test profiles database 400 can be traversed and compared with the profile for production component 60 and a determination as to which of the plurality of test profiles most closely matches the production profile can be made. In doing so, profile comparator module 32 can determine whether production component 60 is defect free, and can determine the attributes (e.g., the size, shape, location and orientation) of any defects present. Specifically, production component 60 would be known to have defects 352A-D matching those known defects 352A-D that are in test component 70 if a test profile that matches the profile of production component 60 is found.

Referring again to FIG. 1, computer system 12 (e.g., remaining life estimator module 38) can estimate, based on the nature of the defect, the remaining life of the production component. To do so, test component 70 can be subjected to stress testing until failure of test component 70 is achieved. This stress testing can then be compared to stress testing of a non-flawed component to determine the difference in durability. Further, test component 70 containing designed defects can be placed into actual service so as to experience the actual loads and operating conditions seen by productions parts. Alternatively, test component 70 could be tested under a specified set of loading conditions designed to simulate the operational environment for the purposes of evaluating the effect(s) of the designed defect(s) on component life without the need to place test component 70 into service. Based on this comparison, an estimation of the impact of the defect on the remaining life of test component 70 can be made. This estimation can be stored in conjunction with the profile of test component 70. Upon a match by profile comparator module 36 of the profile of test component 70 with a profile of production component 60, the estimation can be retrieved and used to estimate the remaining life of production component 60.

While shown and described herein as a method and system for configuring software for an electric meter, it is understood that aspects of the invention further provide various alternative embodiments. For example, in one embodiment, the invention provides a computer program fixed in at least one computer-readable medium, which when executed, enables a computer system to configuring software for an electric meter. To this extent, the computer-readable medium includes program code, such as engineering component analyzing program 30 (FIG. 1), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as engineering component analyzing program 30 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for configuring software for an electric meter. In this case, a computer system, such as computer system 12 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for analyzing an engineering component, comprising:

analyzing the engineering component to obtain a production profile;

manufacturing a test component having a known defect, the known defect being a flaw that is intentionally included in the test component;

analyzing the test component to obtain a test profile of the defect;

comparing the production profile and the test profile to determine whether the engineering component has a defect that corresponds to the known defect;

applying a structural test to the test component to achieve a failure of the test component; and estimating, based on the structural test, an impact of the defect on a remaining life of the engineering component.

2. The method of claim 1, further comprising:
prior to the manufacturing:
   analyzing a production engineering component to obtain a production component defect; and
   designing the test component in such a way that the known defect matches the production component defect.

3. The method of claim 1, wherein the analyzing is performed using an analyzer that is selected from the group, comprising: an acoustic device, an electromagnetic device, a radiographic device, a vision-based device or a liquid penetrant device.

4. The method of claim 1, further comprising:
storing the test profile in a database, the database having a plurality of test profiles, every test profile corresponding to a distinct test defect; and
determining, based on the comparing, which of the plurality of test profiles most closely matches the production profile.

5. The method of claim 1, wherein the manufacturing includes use of an additive manufacturing process.

6. A system for analyzing an engineering component, comprising:
a test component manufactured having a known defect, the known defect being a flaw that is intentionally included in the test component;
an analyzer that analyzes the test component to obtain a test profile of the defect and analyzes the engineering component to obtain a production profile;
a comparator that compares the production profile and the test profile to determine whether the engineering component has a defect that corresponds to the known defect;
a structural tester that applies a structural test to the test component to achieve a failure of the test component; and
an estimator that estimates, based on the structural test, an impact of the defect on a remaining life of the engineering component.

7. The system of claim 6, wherein the analyzer further analyzes a production engineering component to obtain a production component defect, and wherein the test component is designed in such a way that the known defect matches the production component defect.

8. The system of claim 6, wherein the analyzer is selected from the group, comprising: an acoustic device, an electromagnetic device, a radiographic device, a vision-based device or a liquid penetrant device.

9. The system of claim 6, further comprising:
a database that stores the test profile, the database having a plurality of test profiles, every test profile corresponding to a distinct test defect; and
a determinator that determines, based on the comparing, which of the plurality of test profiles most closely matches the production profile.

10. The system of claim 6, wherein the test component is manufactured using an additive manufacturing process.

11. A program product stored on a computer readable storage medium for analyzing an engineering component, which when executed by a computer, performs a method, comprising:
analyzing the engineering component to obtain a production profile;
directing a manufacture of a test component having a known defect, the known defect being a flaw that is intentionally included in the test component;
analyzing the test component to obtain a test profile of the defect;
comparing the production profile and the test profile to determine whether the engineering component has a defect that corresponds to the known defect;
applying a structural test to the test component to achieve a failure of the test component; and
estimating, based on the structural test, an impact of the defect on a remaining life of the engineering component.

12. The program product of claim 11, the method further comprising:
prior to the directing:
   analyzing a production engineering component to obtain a production component defect; and
   designing the test component in such a way that the known defect matches the production component defect.

13. The program product of claim 11, wherein the analyzing is performed using an analyzer that is selected from the group, comprising: an acoustic device, an electromagnetic device, a radiographic device, a vision-based device or a liquid penetrant device.

14. The program product of claim 11, the method further comprising:
storing the test profile in a database, the database having a plurality of test profiles, every test profile corresponding to a distinct test defect; and
determining, based on the comparing, which of the plurality of test profiles most closely matches the production profile.

15. The program product of claim 11, wherein manufacture includes use of an additive manufacturing process.

16. A method for providing a test engineering component, comprising:
determining a first profile that defines a baseline engineering component corresponding to the test engineering component;
determining a second profile having data that define a known defect, the known defect being a flaw that deviates from the baseline component in a known manner;
manufacturing the test engineering component having the known defect using an additive manufacturing process based on the first profile and the second profile;
applying a structural test to the test engineering component to achieve a failure of the test engineering component; and
estimating, based on the structural test, an impact of the defect on a remaining life of a production engineering component.

17. The method of claim 16, further comprising:
analyzing the test component to obtain a test profile having the defect;
analyzing the production engineering component to obtain a production profile; and comparing the production profile and the test profile to determine whether the engineering component has a defect that corresponds to the known defect.

\* \* \* \* \*